United States Patent [19]
Gross

[11] Patent Number: 5,565,979
[45] Date of Patent: Oct. 15, 1996

[54] SURFACE SCANNING APPARATUS AND METHOD USING CROSSED-CYLINDER OPTICAL ELEMENTS

[75] Inventor: Kenneth P. Gross, San Carlos, Calif.

[73] Assignee: Tencor Instruments, Mountain View, Calif.

[21] Appl. No.: 334,522

[22] Filed: Nov. 4, 1994

[51] Int. Cl.$^6$ .......................... G01N 21/00; G01N 21/84; G01B 9/08
[52] U.S. Cl. ...................... 356/237; 356/431; 356/398
[58] Field of Search .................... 356/237, 371, 356/398, 431; 250/234, 236

[56] References Cited

U.S. PATENT DOCUMENTS

| | | | |
|---|---|---|---|
| 4,938,601 | 7/1990 | Weber | 356/431 |
| 5,076,692 | 12/1991 | Neukermans et al. | 356/539 |
| 5,125,741 | 6/1992 | Okada et al. | 356/237 |
| 5,168,386 | 12/1992 | Galbraith | 359/215 |
| 5,416,594 | 5/1995 | Gross et al. | 356/237 |

*Primary Examiner*—Richard A. Rosenberger
*Assistant Examiner*—Robert Kim
*Attorney, Agent, or Firm*—Majestic, Parsons, Siebert & Hsue

[57] ABSTRACT

An apparatus and method for inspecting a substrate, such as a semiconductor wafer, includes crossed cylindrical optical elements that form an elliptical beam that is caused to scan in parallel fashion at an oblique angle to the substrate. Preferably, the smaller dimension of the elliptical beam is perpendicular to the direction of the scan of the beam across the wafer. A reflector converts an angularly varying beam to a telecentrically scanning beam and also provides focusing only in the direction parallel to the telecentric scan. On the other hand, a cylinder lens has a focusing power only in the direction perpendicular to the telecentric scanning.

12 Claims, 2 Drawing Sheets

SURFACE SCANNING APPARATUS AND METHOD USING CROSSED-CYLINDER OPTICAL ELEMENTS

TECHNICAL FIELD

The present invention relates generally to devices and methods for inspecting surfaces and more particularly to optics of such devices and methods.

BACKGROUND ART

Manufacturing yield in the fabrication of integrated circuits and micromachine devices can be increased by first inspecting one or both major surfaces of a semiconductor wafer from which the circuits or devices are fabricated. Surface inspection of semiconductor wafers and the like may also take place at various subsequent stages of a fabrication process. A typical surface inspection apparatus includes an optical system that causes a light beam to scan across a surface of the substrate of interest. Information regarding the surface is determined by processing data related to the reflection or scattering of light from the surface.

U.S. Pat. No. 5,076,692 to Neukermans et al. describes an optical system having a laser source and optical elements for scanning a semiconductor wafer. A deflection mirror pivots on a spindle to cause a beam from the laser source to strike a lens in a scanning fashion. The scan from the deflection mirror to the lens is one in which the scan is a continuous change in the angle of the beam to the lens. On the other hand, the lens causes the beam to scan "telecentrically," i.e. the beam remains parallel to an arbitrary reference plane as the scanning progresses. Neukermans et al. describes the telescanning beam as having an angle of incidence of approximately seventy to eight-five degrees with respect to the normal of the surface of interest.

Telecentricity is designed to eliminate the variation in angle of incidence of the laser beam as the beam scans from one edge to the opposite edge of the surface of interest. Telecentric scanning is also described in U.S. Pat. No. 5,168,386 to Galbraith. The Galbraith patent describes use of an off-axis concave spherical mirror to achieve a telecentric scan, rather than a lens as taught by Neukermans et al. The spherical mirror, in combination with other correcting optics, can be used to achieve a uniformly focused circular beam having a desired diameter upon intersection with the surface of interest. Galbraith teaches that a typical focused spot size of 20 µm can be maintained in a flat field scan over the length of a standard semiconductor wafer, i.e. 200 mm.

As previously noted, the angle of incidence of the circular beam is taught by Neukermans et al. as being within the range of seventy to eight-five degrees with respect to the normal of the surface of interest. An oblique angle of incidence is common in the art. Galbraith teaches that the scan should be substantially "flat field," i.e. imaging in a plane coinciding with the surface of interest.

A difficulty with the prior art techniques of inspecting a surface is that the techniques are susceptible to the effects of optical aberrations which tend to distort the beam. Galbraith teaches that there are difficulties in minimizing or eliminating astigmatism and coma. Particularly where the angle of incidence is shallow relative to the surface of interest, astigmatism may be an issue in the attempt to optimize the inspection process. Regardless of the angle of incidence, there is an issue of distortion introduced because the spherical mirror of Galbraith is off-axis. The beam from the off-axis spherical mirror will be somewhat distorted at the opposed extremes of the scan, in the absence of a correction mechanism.

Potentially, reliability is further reduced by use of a parabolic cylinder mirror to form a telecentrically scanning beam across a surface, as taught in U.S. Pat. No. 5,125,741 to Okada et al. The parabolic cylinder mirror of Okada et al. is aligned so that the path of an incoming beam follows the curvature of the mirror. The curvature creates the desired telecentric scan, but also focuses the beam in the direction of the scan. Consequently, the beam that strikes the surface of interest is strongly astigmatic, with a long dimension in the direction perpendicular to the direction of scan. Because the elliptical beam strikes the surface at a shallow angle of incidence, the beam is further elongated. The Okada et al. patent was designed for use in industrial fields, such as automobiles and appliances. While the Okada et al. apparatus works well in the fields for which it was designed, the apparatus is likely unusable in applications such as detecting defects and/or particles that are measured in microns or submicrons.

An object of the present invention is to provide an apparatus and method for telecentrically scanning a surface of interest in a manner to improve the inspection characteristics of an inspection instrument, such as an instrument for quality control measurements in the manufacture of semiconductor substrates.

SUMMARY OF THE INVENTION

The above object has been met by an apparatus and method in which a beam is dimensionally tailored by first and second optical elements, with one optical element providing focusing substantially only in a direction of beam scan and the other optical element providing focus only in the orthogonal direction. Because the orthogonal optical powers are separated, the optical elements may be off-axis, i.e. not coaxial, to an incoming beam without introducing distortions during scanning of the beam. Off-axis placement reduces obscuration.

In the preferred embodiment, the optical elements combine to form an elliptical beam for which the smaller dimension is perpendicular to the direction of scan. Thus, as the elliptical beam is caused to impinge a surface of interest at an oblique angle, the beam footprint is elongated as a trigonmetric function of the angle of incidence. That is, the smaller dimension of the elliptical beam is elongated upon striking the surface of interest. However, in some applications the smaller dimension is parallel to the direction of scan.

The apparatus and method are well suited for inspecting a surface of a semiconductor wafer. The wafer is positioned on a support that preferably can be moved relative to the optical elements. The elliptical beam impinges the wafer at an oblique angle. One of the optical elements is an off-axis reflector, preferably a cylinder mirror, that converts an angularly scanning beam into a light beam that scans in a parallel fashion, i.e., scans telecentrically. The other of the two optical elements is a cylinder lens that provides the orthogonal focusing. The reflector and the lens are crossed cylinders in the preferred embodiment. That is, the cylinder lens has a curvature that is at a substantially 90° angle relative to a curvature of the reflector.

In one embodiment, which could be used to produce a circular beam footprint, the parallel scanning beam has an angle of incidence of approximately 70° relative to the normal of the surface of the wafer. Prior to impingement, the beam spot size is 40 µm×20 µm, with the larger dimension being parallel to the direction of beam spot scanning across the wafer. Because the impingement is at a 70° angle relative to the normal of the surface, the footprint of the beam upon impingement is increased by a factor of 2.92 in the direction orthogonal to the direction of beam spot scanning. Thus, the desired ellipticity depends on a number of factors, including the angle of incidence. It is noted that a beam spot of approximately 40 µm×14 µm would provide a circular beam footprint.

The reflector and the cylinder lens have common focal points, but this is not critical. The reflector preferably is one focal length away from a scanner that defines the angularly deflecting scanning beam.

An advantage of the invention is that the cross cylinder arrangement provides a telecentric flat-field scan that is close to the diffraction-limited performance of a surface inspection device. The invention provides compensation for the distortions specified in U.S. Pat. No. 5,168,386 to Galbraith by separating beam focusing into separate orthogonal optical powers.

BEST MODE FOR CARRYING OUT THE INVENTION

Figure 1:
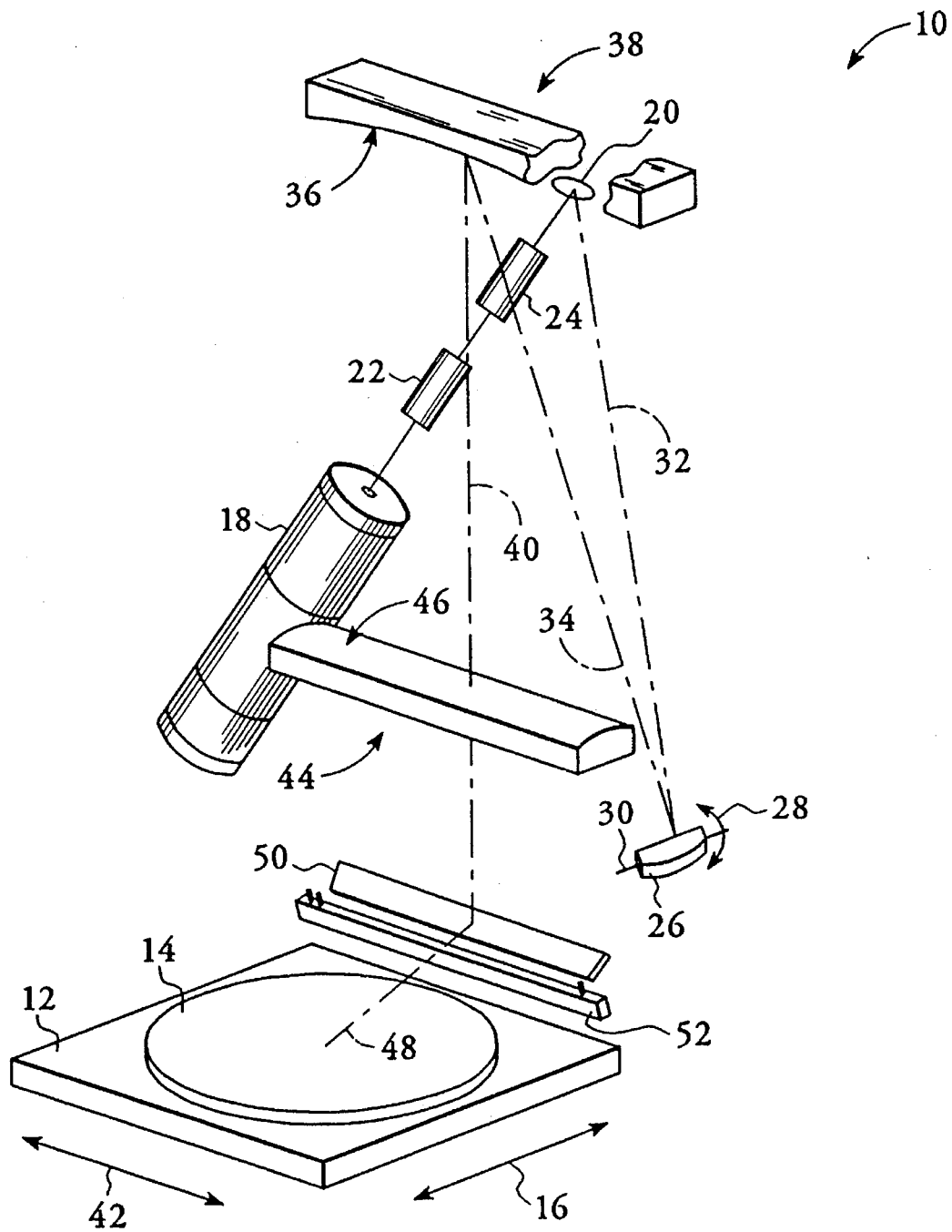
FIG. 1 is a perspective view of a preferred embodiment of a surface scanner in accordance with the invention.

With reference to FIG. 1, a surface scanner 10 is shown as including a support 12 for a semiconductor wafer 14. The surface scanner may be used for detecting particles on the upper surface of the wafer, or may be employed to measure film thickness, surface haze or reflectivity of the wafer. Although the scanner is particularly suited for use in characterizing semiconductor wafers, the scanner may be used with similar substrates.

The support 12 may include a robotic gripper, not shown, for selectively moving the wafer 14 relative to the optical elements to be described below. Movement is typically linear, as shown by arrow 16. The position of the support is computer monitored and is precisely controlled by a motor. The particular form of transport is not important to the invention.

A single wavelength laser 18 generates a light beam that is reflected by a beam-folding mirror 20. Preferably, the laser is a high power, short wavelength radiation source, such as an argon or HeCd gas laser. A suitable output power is 30 milliwatts or greater. Prior to reaching the beam-folding mirror 20, the beam from the laser 18 passes through an optical polarizer module 22 and through expansion and filtering optics 24. The polarizer module contains several optical elements that establish a desired polarization state of the light beam. The elements of the modules may be adjustable, with motors and/or actuators that rotate or translate the elements into or within the light beam to create the desired polarization state. Three input polarizations of particular interest are P-polarization alignment that is parallel to the plane of incidence, S-polarization that is aligned perpendicular to the plane of incidence, and circular polarization that is characterized by continuously alternating between P-polarization and S-polarization at the frequency of the lightwave.

The appropriately polarized beam is then expanded and spatially filtered at the optics 24. Consequently, a circular shaped beam impinges the beam-folding mirror 20 and is directed to a scanner mirror 26. The mirror oscillates about an axis 30, as indicated by arrow 28. A galvanometer motor, not shown, may be used to oscillate the scanner mirror in a manner known in the art.

The scanner mirror 26 is conventionally supported by crossed flexures and is driven by an induction torque driver. The scanner mirror converts the circular shaped light beam from a fixed path 32 to an angularly deflecting beam 34 which traces out a shallow cone. The scanning beam 34 follows a curved path along the curved surface 36 of an off-axis cylinder reflector 38. Oscillation of the scanner mirror 26 about the axis 30 causes the angularly deflecting beam 34 to scan in a generally parallel fashion, i.e. nearly telecentrically, after reflecting from the curved underside of the cylinder reflector. In the same manner as the spherical mirror of U.S. Pat. No. 5,168,386 to Galbraith, the cylinder reflector 38 of FIG. 1 is off-axis and is configured to convert the angularly deflecting beam 34 to a telecentric beam 40. However, an important difference between the cylinder reflector 38 and the spherical mirror of Galbraith is that the cylinder reflector of FIG. 1 provides focusing only in a plane that is parallel to the direction of beam spot scanning of the telecentric beam 40. This is shown graphically in FIG. 2. The cylinder reflector is impinged by the circular beam 34, but has a focusing power that acts to reduce the dimension of the telecentric beam 40 parallel to the scan direction indicated by arrow 42.

The curved surface 36 of the cylinder reflector 38 has the radius of curvature selected to achieve the telecentric scanning. The distance between the scanner mirror 26 and the curved surface 36 should be equal to the effective focal length of the telecentric optical system. In practice, the focal length is approximately one-half of the radius of curvature of the curved surface, typically approximately 500 mm.

The cylinder reflector 38 is positioned off-axis of the angularly deflecting beam 34 that reaches the curved surface 36. This off-axis configuration allows the telecentric beam 40 to proceed without obscuration.

Figure 2:
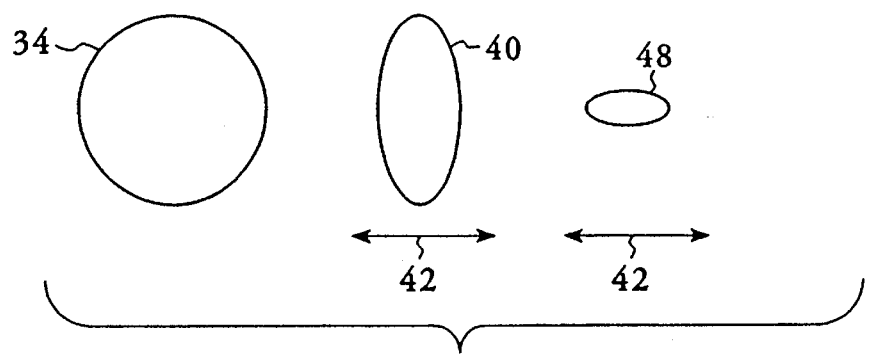
FIG. 2 is a series of cross sections of beams formed using the surface scanner of FIG. 1.

A second cylinder element 44 provides focusing in a direction orthogonal to the focusing by the cylinder reflector 38. The second cylinder element is a lens 44 that has a curved upper surface 46 that defines the focusing power in a single direction. The focusing power is normal to the telecentric beam scan. While the lens 44 is shown as being plano-convex, other embodiments in the optical element having the desired focusing characteristics may be used. As shown in FIG. 2, the cylinder lens 44 will act to provide an elliptical beam 48 at the substrate, with the smaller dimension of the elliptical beam being the dimension that is measured perpendicular to the beam scan 42.

The telecentrically scanning elliptical beam 48 is directed by a plane mirror 50 toward the surface of the semiconductor wafer 14. Optionally, the beam also passes a bar 52 that supports a number of precisely positioned marker pens for establishing the position of the beam. The use of marker pens for this purpose is known in the art.

The distance between the cylinder lens 44 and the cylinder reflector 38 determines the size of the smaller dimension of the elliptical beam 48 prior to impingement upon the surface of the semiconductor wafer 14. The ability to selectively vary the smaller dimension provides advantages in some applications. For example, the throughput for a quality control process can be increased by increasing spot size, since the larger spot increases the area coverage per scan. As another example, a preliminary inspection of a substrate can be performed in order to determine whether a more exacting inspection is appropriate. However, an increase in spot size typically will be accompanied by a sacrifice in precision. Movement of the cylinder lens of a given focal length from the "focused" position, either toward or away from the cylinder reflector, will increase the size of the beam dimension perpendicular to the direction of beam spot scanning. In the preferred embodiment, the focal length of the lens 44 is chosen to produce a focused spot dimension (perpendicular to the beam spot scanning direction) of approximately 20 μm at the wafer surface. The lens position depends on both the focal length of the cylinder mirror 38 and the optical path length chosen between the mirror and the wafer surface 14. In practice, the distance between the cylinder lens and the surface of the semiconductor wafer is somewhat longer than the focal length of the lens.

In a preferred embodiment, the angle of incidence is approximately seventy degrees relative to the normal of the surface of the semiconductor wafer 14. As is known in the art, the diffusely or specularly reflected light from the wafer surface can be monitored, with the resulting data being used to determine characteristics regarding the wafer surface. For example, the presence of particulate matter may be detected using the data related to scattered energy. Particle detection of this type is more thoroughly described in the above-cited patent to Neukermans et al., which is assigned to the assignee of the present invention.

In FIG. 2, the shorter dimension of the elliptical beam 48 prior to wafer impingement is preferably 20 μm. The larger dimension, which is parallel to the scan direction 42, may be 40 μm. However, since the beam strikes the surface obliquely, the footprint of the beam on the wafer surface is elongated in the direction normal to the beam spot scan direction. At an angle of twenty degrees to the surface of the wafer, the footprint is elongated as a cosine function of the angle to the normal, i.e. 1/cos (70°)=2.92.

By splitting the orthogonal optical powers, the invention reduces beam distortions such as astigmatism and field curvature. Such beam distortions are typically encountered in scanning systems such as the one described in the Galbraith patent, in which optical power is derived from a single fixed spherical surface that is off-axis and that is associated with the moderately high numerical apertures needed to achieve a circular shaped spot having a diameter in the neighborhood of 20 μm to 40 μm.

The preferred dimensions of the elliptical beam 48 prior to impingement will therefore depend upon such factors as the angle of incidence. Preferably, the spot size ellipticity is between 1.5 and 3.0.

Figure 3:
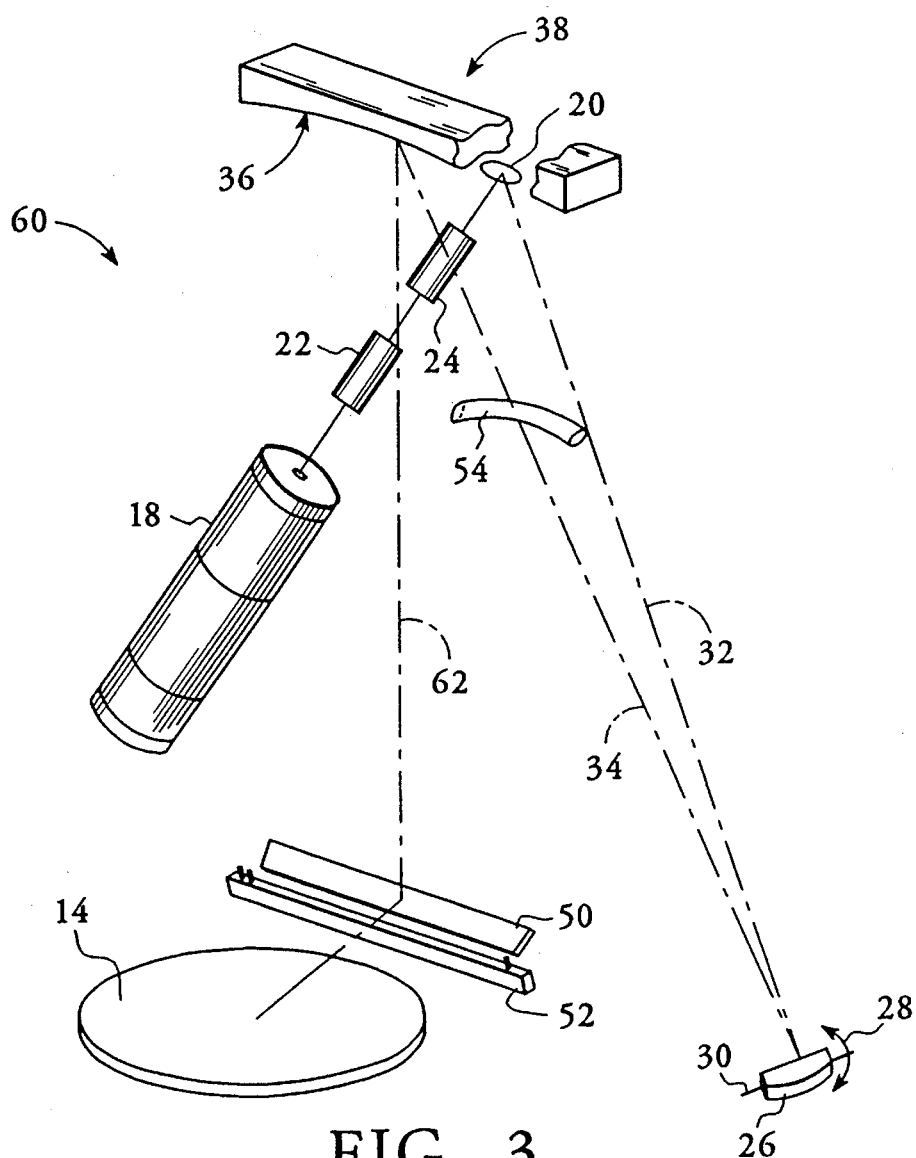
FIG. 3 is a perspective view of a second embodiment of a beam scanner in accordance with the invention.

Referring now to FIG. 3, a second embodiment of the invention places a cylinder lens 54 before a cylinder reflector 38. By placing the cylinder lens 54 before the reflector, the optical elements can easily form an elliptical beam having a smaller dimension that is parallel to the scan direction along a semiconductor wafer 14. That is, the orientation of the elliptical beam is a rotation of 90° relative to the beam produced by the embodiment of FIG. 1.

The cylinder lens 54 of FIG. 3 is more complex than the plano-convex lens described above. The cylinder lens 54 is curved in order to maintain a normal angle of incidence for the scanning beam as the scanner mirror 26 is caused to rotate. The cylinder lens may be toroidal, with appropriate cylinder surfaces, so as to provide a net focusing power of approximately zero in the scan direction and a substantial focusing power in the orthogonal direction. That is, the cylinder lens does not significantly affect either the direction of travel from the scanner mirror 26 to the cylinder reflector 38, or the focus in the scan direction.

Components of the surface scanner 60 of FIG. 3 that are identical to the scanner 10 of FIG. 1 have the same reference numerals. The laser 18 directs a light beam through a polarizer module 22 and through expansion and filtering optics 24 to impinge a beam-folding mirror 20. Reflection from the beam-folding mirror defines a fixed light path 32 to the scanner mirror. Oscillation of the scanner mirror about axis 30 defines an angularly propagating beam path 34. The beam along the path 34 is focused in one direction by the cylinder lens 54. Focusing in the orthogonal direction is provided by the cylinder reflector 38, which also acts to convert the angularly propagating beam to a telecentrically propagating beam 62. A plane mirror 50 is used to direct the beam 62 at an oblique angle relative to the surface of the semiconductor wafer 14. A bar 52 includes alignment markings that may be used to monitor the position of the beam 62.

While the embodiment of FIG. 3 may be desirable in some applications, the surface scanner 10 of FIG. 1 is preferred. The telecentric beam 48 of FIG. 1 has an ellipticity that is designed to limit the size of the beam footprint on the surface in the direction parallel to the wafer movement, and overcomes problematic beam distortions experienced in the prior art. Preferably, the spot size ellipticity of the beam 48 immediately adjacent to impingement with the semiconductor wafer 14 is in the range of 1.5 to 3.0. The desired ellipticity will depend on such factors as the angle of incidence to the semiconductor wafer.

I claim:

1. An apparatus for inspecting a substrate comprising:

a support for positioning said substrate;

optical means for directing an incoming parallel light beam onto a surface of said substrate at a substantially fixed oblique angle of incidence relative to said surface, thereby defining a generally linear beam scan path across said surface, said optical means including a cylindrical optical member having a first focusing power substantially only in a direction perpendicular to said beam scan path, reflector means for transforming an angularly scanning beam into a light beam scanning in a parallel fashion, said reflector means being positioned relative to said optical means to direct said parallel scanning light beam to said optical means, said reflector means having a second focusing power substantially only in a direction parallel to said beam scan path across said surface; and source means for generating a generally circular, angularly scanning beam to be transformed into said parallel scanning light beam by said reflector means;

wherein said reflector means receives said generally circular, angularly scanning beam and provides said parallel scanning light beam to said optical means, with said reflector means reducing the dimension of said beam in a first direction and said optical means reducing the dimension of said beam in a second direction perpendicular to said first direction, wherein said cylindrical optical member and said reflector means form a crossed cylinders arrangement in which focusing power in said direction perpendicular to said beam scan path is greater than focusing power in said direction parallel to said beam scan path, thereby presenting an elliptical beam at the surface of said substrate, with said elliptical beam having a smaller dimension being perpendicular to said beam scan path.

2. The apparatus of claim 1, further comprising means for adjusting the relative positions of said cylindrical optical member and said reflector means, wherein adjusting the relative positions changes the ellipticity of said elliptical beam.

3. The apparatus of claim 1 wherein said reflector means is a cylinder mirror having a curvature perpendicular to a curvature of said cylindrical optical member of said optical means.

4. The apparatus of claim 1 wherein said source means includes a light source positioned to define an optical axis, said source means further including an oscillating deflector positioned on said optical axis.

5. The apparatus of claim 1 wherein said support for positioning said substrate is a semiconductor wafer support member, said apparatus further comprising means for displacing said wafer support member in a direction perpendicular to said beam scan path.

6. The apparatus of claim 1 wherein said reflector means is a concave cylinder mirror and wherein said cylindrical optical member is a convex cylinder lens having a curvature that is perpendicular to a curvature of said concave cylinder mirror.

7. An apparatus for inspecting a surface of a substrate comprising:

a source of a light beam having an optical axis, said light beam having a substantially circular shape in a cross section perpendicular to said optical axis;

scanning means positioned on said optical axis for angularly deflecting said light beam to sweep along a first beam propagation path;

crossed cylinders means for converting said angularly deflecting light beam from said scanning means into a scanning elliptical beam in which said light beam remains at a fixed angle relative to an arbitrary reference plane, said crossed cylinders means including a cylinder lens and a cylinder mirror, said cylinder lens having a curvature at a substantially 90° angle to a curvature of said cylinder mirror, said cylinder lens having focusing power substantially limited to focusing in a direction to reduce the beam dimension that is perpendicular to a scanning direction of said elliptical beam, said cylinder mirror having focusing power substantially limited to focusing in a direction to reduce the beam dimension that is parallel to said scanning direction, wherein said crossed cylinders means is such that focusing power in said direction perpendicular to said scanning direction is greater than focusing power in said direction parallel to said scanning direction, thereby presenting an elliptical beam at the surface of said substrate, with said elliptical beam having a smaller dimension being perpendicular to said scanning direction; and support means for supporting said substrate at an oblique angle to said elliptical beam.

8. The apparatus of claim 7 wherein said cylinder lens is disposed between said cylinder mirror and said support means.

9. The apparatus of claim 7 wherein said scanning means is an oscillating deflector.

10. A method of inspecting a surface of a substrate comprising the steps of:

generating a light beam;

deflecting said light beam to form a scanning beam pattern of an angularly varying beam;

deflecting said angularly varying light beam to form a second scanning beam pattern such that said light beam remains at a fixed angle to an arbitrary reference plane, thereby forming a substantially telecentrically scanning beam, said deflecting step comprising deflecting the beam along a surface, the scanning beam pattern intersecting the surface along a beam scan path, the deflecting step including focusing the beam substantially only in a direction parallel to said beam scan path across said surface;

an additional focusing step including focusing the beam substantially only in a direction perpendicular to said beam scan path across said surface of the reflector; and projecting the beam onto the surface of the substrate;

wherein the focusing and additional focusing steps are such that focusing power in said direction perpendicular to said beam scan path is greater than focusing power in said direction parallel to said beam scan path, thereby presenting an elliptical beam at the surface of said substrate, with said elliptical beam having a smaller dimension being perpendicular to said beam scan path.

11. The method of claim 10, wherein said additional focusing step is done after the step of focusing the beam substantially only in a direction parallel to said beam scan path across said surface.

12. The method of claim 10 wherein the deflecting step that produces the telecentric scanning beam includes projecting said angularly varying light beam onto a cylinder mirror having focusing power only parallel to said scanning direction of said second scanning beam pattern.

* * * * *